United States Patent
Xu et al.

(10) Patent No.: US 10,017,489 B2
(45) Date of Patent: Jul. 10, 2018

(54) METHOD FOR PREPARING BENZOPYRAN COMPOUND AND APPLICATION THEREOF IN TREATING PULMONARY FIBROSIS

(71) Applicant: SHANGHAI JIAO TONG UNIVERSITY, Shanghai (CN)

(72) Inventors: Minjuan Xu, Shanghai (CN); Jun Xu, Shanghai (CN); Zhigang Zhang, Shanghai (CN); Yahui Wang, Shanghai (CN)

(73) Assignee: SHANGHAI JIAO TONG UNIVERSITY, Shanghai (CN)

( * ) Notice: Subject to any disclaimer, the term of this patent is extended or adjusted under 35 U.S.C. 154(b) by 55 days.

(21) Appl. No.: 14/904,695

(22) PCT Filed: Apr. 21, 2014

(86) PCT No.: PCT/CN2014/075773
§ 371 (c)(1),
(2) Date: Jan. 12, 2016

(87) PCT Pub. No.: WO2015/035778
PCT Pub. Date: Mar. 19, 2015

(65) Prior Publication Data
US 2016/0185742 A1    Jun. 30, 2016

(30) Foreign Application Priority Data

Sep. 13, 2013  (CN) .......................... 2013 1 0419778

(51) Int. Cl.
*C07D 311/00* (2006.01)
*C07D 311/58* (2006.01)
(Continued)

(52) U.S. Cl.
CPC ............ *C07D 311/58* (2013.01); *C12P 17/06* (2013.01); *C12R 1/465* (2013.01)

(58) Field of Classification Search
CPC ........ C07D 311/58; C12R 1/465; C12P 17/06
(Continued)

(56) References Cited

FOREIGN PATENT DOCUMENTS

JP      2000-72766      3/2000

OTHER PUBLICATIONS

PCT-237 p. 1-8 (2014).*
(Continued)

*Primary Examiner* — Taylor V Oh

(57) ABSTRACT

The present invention opens to the public a method to prepare a benzopyran compound and its use for treating pulmonary fibrosis. A benzopyran compound has a structure (I):

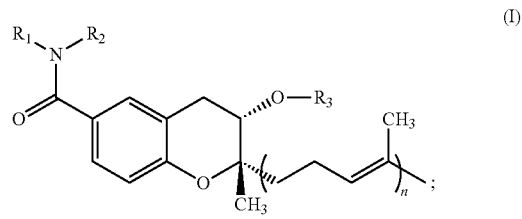

in which: R1 represents hydrogen, C1-C4 alkyl, or various remaining amino acid moieties after removal of an amino group; R2 represents hydrogen, C1-C4 alkyl, or various remaining amino acid moieties after removal of an amino group; R3 represents hydrogen, or C1-C4 alkyl; and n is any integer of 1-4, wherein the benzopyran compound is derived from a broth of *Streptomyces xiamenensis* CGMCC No. 5675 by extraction, separation and purification. The derivatives of xiamenmycin made from the present invention have a higher bioactivity to suppress the proliferation of normal (Continued)

human lung fibroblast, and medicinal products containing the same are useful in the treatment of pulmonary fibrosis.

2 Claims, 1 Drawing Sheet

(51) Int. Cl.
*C12P 17/06* (2006.01)
*C12R 1/465* (2006.01)

(58) Field of Classification Search
USPC .......................................................... 549/399
See application file for complete search history.

(56) References Cited

OTHER PUBLICATIONS

Xu, MJ. et al. Identification and Characterization of an Anti-Fibrotic Benzopyran Compound Isolated from Mangrove-Derived Streptomyces xiamenensis. Marine Drugs. 2012, vol. 10, p. 639.*
Min-Juan Xu et al. Identification and Characterization of an Anti-Fibrotic Benzopyran Compound Isolated from Mangrove-Derived *Streptomyces xiamenensis.* Marine Drugs. 2012, 10, 639-654, ISSN 1660-3397.
Xiao-Jin Liu et al. Xiamenmycin Attenuates Hypertrophic Scars by Suppressing Local Inflammation and the Effects of Mechanical Stress. Journal of Investigative Dermatology. Jan. 10, 2013; p. 1-19.

\* cited by examiner

METHOD FOR PREPARING BENZOPYRAN COMPOUND AND APPLICATION THEREOF IN TREATING PULMONARY FIBROSIS

CROSS REFERENCE OF RELATED APPLICATION

This is a U.S. National Stage under 35 U.S.C 371 of the International Application PCT/CN2014/075773, filed Apr. 21, 2014, which claims priority under 35 U.S.C. 119(a-d) to CN 201310419778.1, filed Sep. 13, 2013.

BACKGROUND OF THE PRESENT INVENTION

Field of Invention

The present invention relates to natural drug chemistry, more specifically, the present invention relates to a new method for preparing a benzopyran compound and an application thereof in treating pulmonary fibrosis as medication.

Description of Related Arts

Some reports about benzopyran compounds (xiamenmycin) are known for us, Japanese patents included are as follows: Kawamura, N.; Tsuji, E.; Watanabe, Y.; Tsuchihashi, K.; Takako, T. Benzopyran derivatives, their manufacture with *Streptomyces* species, and their use for treatment of asthma and rheumatoid arthritis. Daiichi Seiyaku Co., Ltd.; Mercian Corp.: Kyoto, Japan, 7 Mar. 2000, and the preferences are included such as [Xu, M. J.; Liu, X. J.; Zhao, Y. L.; Liu, D.; Xu, Z. H.; Lang, X. M.; Ao, P.; Lin, W. H.; Yang, S. L.; Zhang, Z. G.; Xu, J., Identification and characterization of an anti-fibrotic benzopyran compound isolated from mangrove-derived *Streptomyces xiamenensis*. *Mar Drugs* 2012, 10, (3), 639-54; Liu, X. J.; Xu, M. J.; Fan, S. T.; Wu, Z.; Li, J.; Yang, X. M.; Wang, Y. H.; Xu, J.; Zhang, Z. G., Xiamenmycin attenuates hypertrophic scars by suppressing local inflammation and the effects of mechanical stress. *J Invest Dermatol* 2013, 133, (5), 1351-60.]. These publications open to us the extraction, isolation and identification of the xiamenmycin, and its inhibitory biological effects on inflammation, fibrosis and hypertrophic scar.

Genetic engineering strain CGMCC No. 5675 is a *Streptomyces xiamenensis* carrying the resistibility of rifamycin and streptomycin. No literature report has been found on benzopyran compounds separated from the strain. As xiamenmycin C (a common name of benzopyran compound of the present invention) loses the side chain of amino acid in comparison with xiamenmycin itself, it is a compound with a novel structure. In the first determination of the activity of that compound for treating pulmonary fibrosis, it was found that it is better than the known compound, xiamenmycin.

SUMMARY OF THE PRESENT INVENTION

A purpose of the present invention is to provide a method for preparing a benzopyran compound and an application thereof in treating pulmonary fibrosis. The present invention discover for the first time that the benzopyran compound can be obtained from the extracts of the genetic engineering *Streptomyces xiamenensis* CGMCC No. 5675.

A strain of the *Streptomyces xiamenensis* as described above has been preserved and deposited in China General Microbiological Culture Collection Center (CGMCC) on Dec. 29, 2011. The preservation address is CAS Microorganism Research Institute, No. 3, Court 1, Beichen West Road, Chaoyang District, Beijing. The culture preservation number is CGMCC No. 5675.

The purpose of the present invention is realized through the following technical scheme.

In a first aspect of the present invention, there is provided a benzopyran compound, as shown in a formula (I):

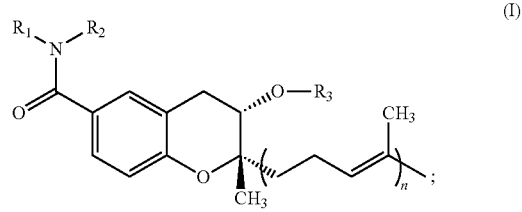

(I)

in which:

$R_1$ represents hydrogen, C1-C4 alkyl group, or various remaining amino acid moieties after removal of an amino group;

$R_2$ represents hydrogen, C1-C4 alkyl group, or various remaining amino acid moieties after removal of an amino group;

$R_3$ represents hydrogen, or C1-C4 alkyl;

n represents any integer of 1-4.

Preferably, the R1 represents hydrogen or methyl, the R2 represents hydrogen or methyl, the R3 represents hydrogen or methyl, with n=1 or 2.

In a further embodiment of the present invention, there is provided a benzopyran compound with the following formula (II):

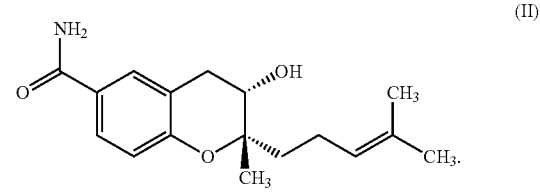 [SMILES: CC(C)=CCC[C@]1(C)Oc2ccc(C(N)=O)cc2C[C@@H]1O]

(II)

In another embodiment of the present invention, there is provided a method for preparation of the benzopyran compound of the formula (II), which includes following steps of:

A) inoculating and culturing *Streptomyces xiamenensis* strain CGMCC No. 5675 in a liquid medium, then extracting and concentrating a broth for a crude extract;

B) subjecting the crude extract to a column chromatography on silica gel, eluting by $CHCl_3$:MeOH (gradient from chloroform:methanol, 100:1, 70:1, 60:1, 50:1, 30:1, 15:1, 10:1, 5:1, 2:1, 1:1 to MeOH) with a rate of 15 second/drop and 200 ml per elution fraction; and C) subjecting the fraction eluted by $CHCl_3$:MeOH (15:1, v:v) from the step B to a column chromatography on Sephadex LH-20 with a rate of 70-90 second/drop and purifying to obtain the benzopyran compound.

Preferably, in step C, the fraction is collected and guided by HPLC fingerprints to find peaks containing a target UV profile (λmax 206, 260 nm), then a combination is purified to obtain the benzopyran compound.

Preferably, in the step A, the extraction of the broth is as follows: the broth is centrifuged to separate a supernatant and a residue; then the supernatant is extracted by ethyl acetate and the residue with a solvent mixture; finally, the extractions from all above are combine; a solvent mixture described above is a mixture of ethyl acetate/methanol/acetic acid (80:15:5, v:v:v).

Preferably, in the step C, purification is as follows, the eluted fraction is collected and purified by HPLC with a mobile phase of acetonitrile/water and by a rate of 45:55 (acetonitrile/water, v:v) to 55:45 (acetonitrile/water, v:v) within 35 minutes.

In another embodiment of the present invention, there is provided an application of the benzopyran compound as hereinbefore defined in preparation of medicinal products for treating pulmonary fibrosis.

Preferably, the present invention provided the application hereinbefore defined for preparing the medicinal products for treating the pulmonary fibrosis, comprising treatments of acute respiratory distress syndrome, acute interstitial pneumonia or chronic acute worsening disease of idiopathic pulmonary fibrosis.

In another embodiment of the present invention, there is provided a medicinal product selected from a group of medicinal products containing the benzopyran compound hereinbefore defined, or its acids or alkalis acceptable in pharmaceutical, or its solvent compound.

The present invention has advantages that:

1. in the present invention, the benzopyran compound is extracted from the culture broth of the genetic engineering *Streptomyces xiamenensis* CGMCC No. 5675 and charactered as the natural medicine;

2. the benzopyran compound reviewed in the present invention possesses the pharmaceutical activity to inhibit normal human lung fibroblasts proliferation and activation with an effective concentration of 15 μg/ml and shows low toxicity to normal human lung fibroblasts;

3. most of conventional drugs used for treating fibrosis are corticosteroids, which have severe side effects for long-term use; whereas, the benzopyran compound in the present invention is different, thus such bioactive small molecule shows great potential for pharmaceutical usage and has a good market application.

BRIEF DESCRIPTION OF THE DRAWINGS

By reading and referring to the detailed description made by the following figures to the non-restrictive embodiment example, other characteristics, purposes and advantages of the present invention will become more apparent.

DETAILED DESCRIPTION OF THE PREFERRED EMBODIMENT

Figure 1:
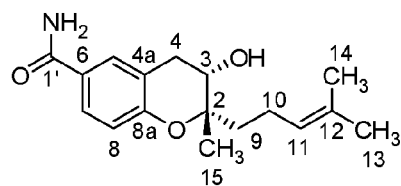
FIG. 1 is a structure of a benzopyran compound—xiamenmycin C of the present invention.

In the following paragraphs, the present invention is described in detail with figures and examples which will assist the technical people in this field to understand the present invention. However, these examples as follows are unable to cover all the present invention. So it should be pointed out that any evolve and improvement made by the skilled person always belong to the scope of the patent protection asked for.

Example 1. Extraction and Purification

*S. xiamenensis* M6 (i.e. *Streptomyces xiamenensis* CGMCC No. 5675) is cultured in a liquid medium (30 liters) for 7 days, then a broth is harvested and centrifuged to separate supernatant and mycelium. The supernatant is partitioned for 3 times by ethyl acetate and a residue is extracted for 3 times by a comparable amount of ethyl acetate/methanol/acetic acid (80:15:5, v:v:v) with 12 hours each time. Total supernatants were combined and concentrated to afford a crude extract (13.4 g). The crude extract is subjected to a column chromatography on silica gel (10 g, 200-300 meshes, produced by Qingdao Ocean Chemical Group Company) with 50 g silica gel, and eluted by $CHCl_3$:MeOH (gradient from chloroform:methanol, 100:1, 70:1, 60:1, 50:1, 30:1, 15:1, 10:1, 5:1, 2:1, 1:1 to MeOH) with a rate of 15 second/drop and 150-100 ml/bottle. Then each fraction (200 ml) eluted by $CHCl_3$:MeOH (15:1, v:v) is subjected to a column chromatography on Sephadex LH-20 with the rate of 70-90 second/drop and eluted by MeOH, then the combination above is isolated by a HPLC (semi-preparative column, C18) with a mobile phase of acetonitrile/water and by a rate of 45:55 (acetonitrile/water, v:v) to 55:45 (acetonitrile/water, v:v) within 35 minutes to obtain a benzopyran compound 1. Next, rest fractions eluted by a solvent mixture of chloroform/methanol, especially eluting ratio near $CHCl_3$:MeOH (15:1, v:v) are also collected. The rest fractions are combined guiding by HPLC fingerprints to find peaks containing a target UV profile (λmax 206, 260 nm) and then the combination is purified by the HPLC (semi-preparative column, C18) with the eluent of acetonitrile/water and the gradient change from acetonitrile:water (45:55, v:v) to acetonitrile:water (55:45, v:v) to obtain a purified benzopyran compound 1, i.e. xiamenmycin C (1.5 mg).

Physical and chemical properties of the compound 1: yellow amorphous powder; $[\alpha]^{26}_D$ +28.45° (c 0.0034, MeOH); UV (MeOH) $\lambda_{max}$=206, 260 nm; CD (c 0.0024, MeOH) $\Delta\varepsilon_{201}$ +12.3, $\Delta\varepsilon_{202}$ +9.6, $\Delta\varepsilon_{205}$ +8.0, $\Delta\varepsilon_{207.4}$ +7.1, $\Delta\varepsilon_{213.6}$ +0.14, $\Delta\varepsilon_{217}$ −1.2, $\Delta\varepsilon_{245.2}$ +2.0, $\Delta\varepsilon_{259.8}$ +3.14, $\Delta\varepsilon_{283}$ +0.03; $^1H$ and $^{13}C$ NMR data, see Table 2; HRESIMS m/z 290.1768 [M+H]$^+$, (calcd for $C_{17}H_{24}NO_3$, m/z 290.1756), 288.1610 [M−H], (calcd for $C_{17}H_{22}NO_3$, m/z 288.2073).

TABLE 1

| | Compound 1 | | |
|---|---|---|---|
| Location | $\delta_H$ (J in Hz) | $\delta_C$, type | HMBC |
| 1 | — | — | — |
| 2 | — | 79.7, C | — |
| 3 | 3.74, dd (7.4, 5.2) | 66.3, CH | 4a, 2, 9, 15 |
| 4 | 2.66, dd (17.3, 7.4) | 31.3, $CH_2$ | 8a, 5, 4a, 2, 3, 6 |
| | 2.93, dd (17.3, 5.2) | | |
| 4a | — | 120.4, C | — |
| 5 | 7.63, d (1.8) | 130.2, CH | 7, 8a, 4, 1' |
| 6 | — | 126.3, C | — |
| 7 | 7.60, dd (8.4, 1.8) | 127.4, CH | 5, 8a, 1' |
| 8 | 6.74, d (8.4) | 116.5, CH | 4a, 8a, 6 |
| 8a | — | 156.0, C | — |
| 9 | 1.59, m | 38.0, $CH_2$ | 11, 12, 2, 3, 10 |
| 10 | 2.10, m | 21.6, $CH_2$ | 11, 12, 2, 9 |
| 11 | 5.10, t (7.3) | 124.8, CH | 13, 10, 14, 9 |
| 12 | — | 131.3, C | — |
| 13 | 1.56, s | 18.0, $CH_3$ | 11, 12, 14 |
| 14 | 1.63, s | 25.9, $CH_3$ | 11, 12, 13 |
| 15 | 1.16, s | 18.8, $CH_3$ | 2, 3, 9 |
| 1' | — | 168.0, C | — |
| 2' | — | — | — |
| 3' | — | — | — |
| 4' | — | — | — |
| 5' | — | — | — |
| 6' | — | — | — |

Signals in Table 1 are based on spectrum analysis results of DEPT, $^1H$-$^1H$ COSY, HMQC and HMBC. Multiplicity of Example 2. Inhibitory Effect of Compound 1 on WI26 Cells Proliferation and Activity Materials:
Cells: Human lung fibroblasts, WI26 cell;
Drug: Compound 1 (Xiamenmycin C), compound 2 (Xiamenmycin) obtained from the above example

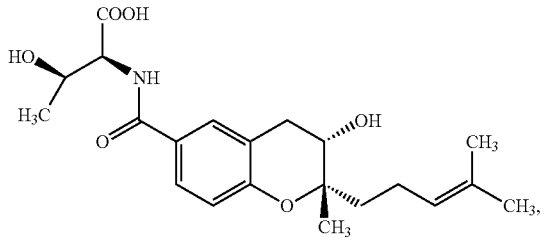 [SMILES: CC(C)=CCC[C@]1(C)Oc2ccc(C(=O)N[C@H](C(=O)O)[C@@H](C)O)cc2C[C@@H]1O]

wherein: a group treated by the compound 1 is a drug treatment group 1 and a group treated by the compound 2 is a drug treatment group 2 for comparison with the compound 1.

Methods: wherein WI26 cells at 70-80% confluent were trysinized by 0.25% trypsin solution and seeded in 96-well plates at an initial density of $1 \times 10^4$ cells/mL. A medium was replaced 24 h later by the fresh with 15 μg/ml compound 1 and 1/1000 DMSO (drug treatment group 1 and its control) or 30 μg/ml compound 2 and 1/1000 DMSO (drug treatment group 2 and its control), then the medium was refreshed and cell viability was measured by using a CCK-8 method at day 0, 1, 2, 3, 4, 5, 6, respectively. Proliferation measurement was applied by adding 100 μL complete medium and 10 μL CCK-8 solutions to each well and incubating for 1 h. OD values of each well were measured at a primary wavelength $\lambda=450$ nm by using a Microplate Spectrophotometer. Data are shown as means±standard deviation (SD) of three independent experiments, each performed in triplicate.

Figure 2:
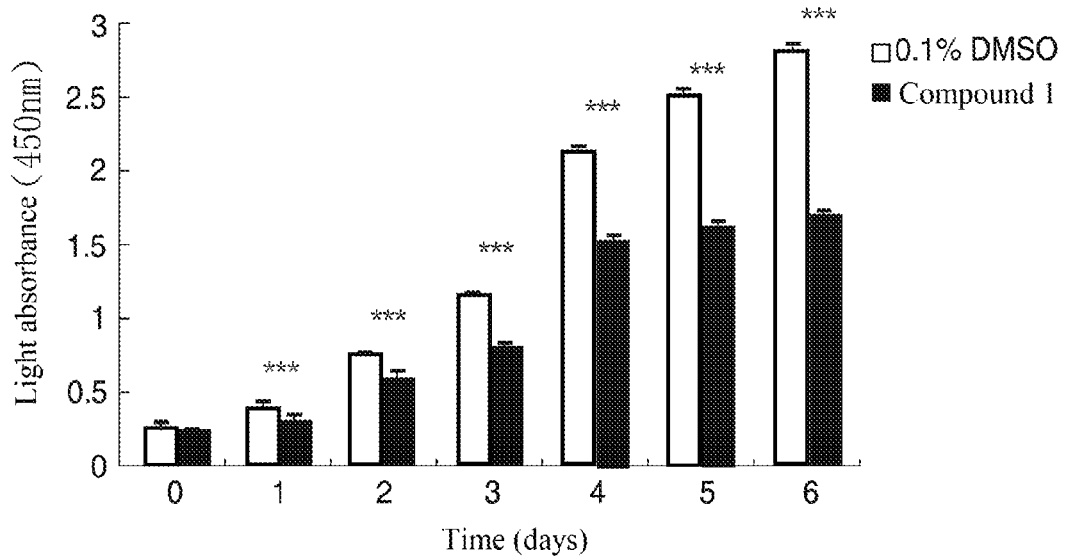
FIG. 2 is a quantification schematic diagram by a CCK-8 assay in an experiment for the benzopyran compound—xiamenmycin C to inhibit human lung fibroblast proliferation.

Results of the experiment are shown as FIG. 2: the compound 1 has an inhibitory effect on WI26 cells proliferation. Inhibition of the WI26 cells exposed to 15 μg/ml compound 1 for day one is 13.8% and day six is 38%. This illuminates that the benzopyran compound hereinbefore defined in the present invention is applicable for preparing drugs treating pulmonary fibrosis. Compared between these two drug treatment groups, an effective concentration of the compound 1 is only half while the inhibition increased near 10%. Therefore the compound 1 has priority in an aspect of the inhibitory effect on the WI26 cells proliferation and activation. Besides, both the compound 1 and the xiamenmycin have a characteristic of low toxicity to cell based on dynamics of the inhibitory effect in FIG. 2. So changing of a side chain of the compound 1 to a higher anti-proliferative effect and low toxicity is a technical difficulty in related field. According to the results above, the skilled person may appreciate that the modifications of the compound 1 (as claimed in claim 1), such as modification of amino acid moiety or increase the side chain, will inevitably bring with itself the considerable activity.

Figure 3:
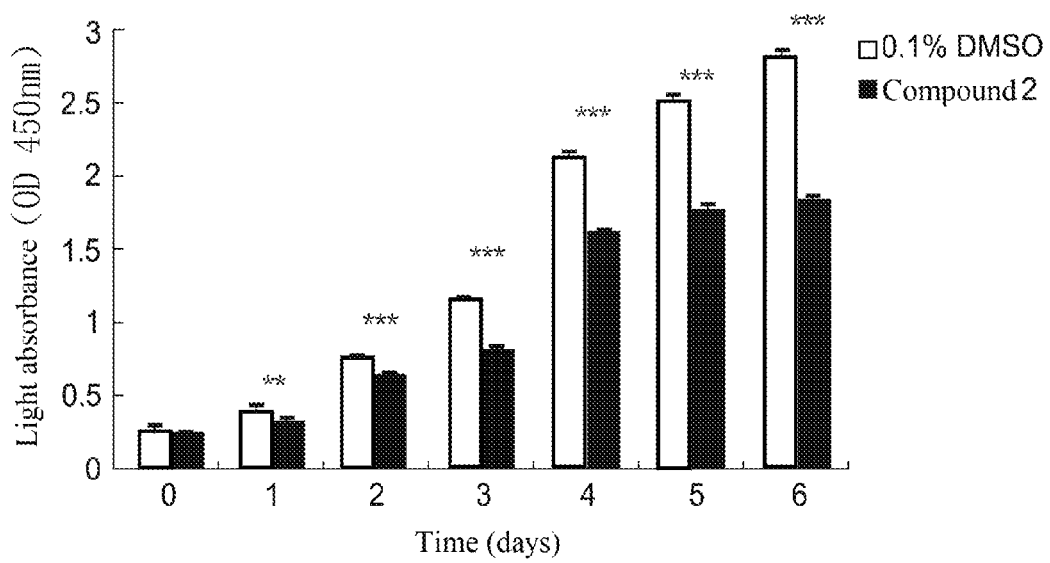
FIG. 3 is a quantification schematic diagram by the CCK-8 assay in the experiment for xiamenmycin to suppress the human lung fibroblast proliferation.

Results of a treatment group 2 (30 μg/ml compound 2 and 1/1000 DMSO) are shown as FIG. 3: the compound 2 has some effects on the WI26 cells proliferation and activation, but a inhibition rate for the day one is 10% and the day six is 28.5%.

The above is a detailed description of the present invention. What needs to understand is that the present invention is not limited to the above specific embodiment. The technical people in this field can make various changes or modifications within the scope of claim and this will not influence the substantial contents of the present invention.

What is claimed is:

1. A preparation method of medicines for treating pulmonary fibrosis, comprising steps of:
   A) inoculating and culturing *Streptomyces xiamenensis* strain DSM 41903 in a liquid medium, then extracting and concentrating a broth for a crude extract; wherein extraction of the broth is as follows: the broth is centrifuged to separate a supernatant and a residue; then the supernatant is extracted with ethyl acetate and the residue with a solvent mixture; finally, the two extractions from all above are combined; and a solvent mixture described above is a mixture of ethyl acetate/methanol/acetic acid 80:15:5, v:v:v;
   B) subjecting the crude extract to a column chromatography on silica gel, eluting by $CHCl_3$:MeOH, 100:1, with a rate of 15 second/drop and 200 ml per elution fraction;
   C) subjecting the fraction eluted by $CHCl_3$:MeOH 15:1, v:v from the step B to a column chromatography on Sephadex LH-20 with a rate of 70-90 second/drop and purifying to obtain a benzopyran compound; wherein the fraction is collected and guided by HPLC fingerprints to find peaks containing a target UV profile λmax 206, 260 nm, then a combination is purified to obtain the benzopyran compound; wherein purification is as follows, the eluted fraction is collected and purified by an HPLC with a mobile phase of acetonitrile/water and by a rate of 45:55 acetonitrile/water, v:v to 55:45 acetonitrile/water, v:v within 35 minutes; and
   D) applying a therapeutically effective amount of the benzopyran compound to the medicines;
   wherein the benzopyran compound is shown in a formula (II):

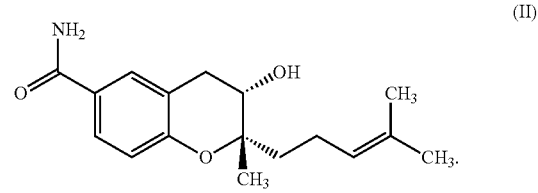 [SMILES: CC(C)=CCC[C@]1(C)Oc2ccc(C(N)=O)cc2C[C@@H]1O]

2. The preparation method as claimed in claim 1 for preparing the medicines for treating the pulmonary fibrosis, comprising treatments of acute respiratory distress syndrome, acute interstitial pneumonia or chronic acute worsening disease of idiopathic pulmonary fibrosis.

* * * * *